(12) United States Patent
Larson et al.

(10) Patent No.: US 12,024,797 B2
(45) Date of Patent: Jul. 2, 2024

(54) METHODS OF PREPARING AND ANALYZING CELL-FREE NUCLEIC ACID SEQUENCING LIBRARIES

(71) Applicant: GRAIL, LLC, Menlo Park, CA (US)

(72) Inventors: Matthew H. Larson, San Francisco, CA (US); Hyunsung John Kim, San Francisco, CA (US); Nick Eattock, Hercules, CA (US); Xiao Yang, San Francisco, CA (US)

(73) Assignee: GRAIL, LLC, Menlo Park, CA (US)

( * ) Notice: Subject to any disclaimer, the term of this patent is extended or adjusted under 35 U.S.C. 154(b) by 380 days.

(21) Appl. No.: 17/133,418

(22) Filed: Dec. 23, 2020

(65) Prior Publication Data

US 2021/0115512 A1   Apr. 22, 2021

Related U.S. Application Data

(62) Division of application No. 16/663,147, filed on Oct. 24, 2019, now Pat. No. 10,907,206, which is a
(Continued)

(51) Int. Cl.
| | |
|---|---|
| *C40B 50/06* | (2006.01) |
| *C12N 15/10* | (2006.01) |
| *C12Q 1/6806* | (2018.01) |
| *C12Q 1/6855* | (2018.01) |
| *C12Q 1/6874* | (2018.01) |

(52) U.S. Cl.
CPC .......... *C40B 50/06* (2013.01); *C12N 15/1065* (2013.01); *C12N 15/1093* (2013.01); *C12Q 1/6806* (2013.01); *C12Q 1/6855* (2013.01); *C12Q 1/6874* (2013.01)

(58) Field of Classification Search
CPC .. C12Q 1/6874; C12Q 1/6806; C12Q 1/6855; C12Q 2525/191; C12Q 2533/101; C12Q 2535/122; C12Q 2565/514; C12Q 2563/179; C12N 15/1065; C12N 15/1093
See application file for complete search history.

(56) References Cited

U.S. PATENT DOCUMENTS

2010/0240101 A1   9/2010   Lieberman et al.

FOREIGN PATENT DOCUMENTS

| | | |
|---|---|---|
| WO | 2009/116863 A2 | 9/2009 |
| WO | 2015/126823 A1 | 8/2015 |

OTHER PUBLICATIONS

Burnham et al. (Scientific Reports vol. 6, Article No. 27859 (2016), p. 1-9, S1-S8).*

(Continued)

*Primary Examiner* — Christian C Boesen
(74) *Attorney, Agent, or Firm* — Haynes and Boone LLP

(57) ABSTRACT

Aspects of the invention relate to methods for preparing and analyzing a sequencing library from a mixed cell-free DNA (cfDNA) sample, wherein the mixed sample includes double-stranded DNA (dsDNA), damaged dsDNA (e.g., nicked dsDNA), and single-stranded DNA (ssDNA) molecules. The subject methods facilitate the collection of information from dsDNA, ssDNA and damaged DNA (e.g., nicked DNA) molecules in a sample, thereby providing enhanced diagnostic information as compared to sequencing libraries that are prepared from dsDNA alone.

13 Claims, 7 Drawing Sheets

Related U.S. Application Data division of application No. 15/713,296, filed on Sep. 22, 2017, now Pat. No. 10,487,358.

(60) Provisional application No. 62/456,029, filed on Feb. 7, 2017, provisional application No. 62/399,167, filed on Sep. 23, 2016.

(56) References Cited

OTHER PUBLICATIONS

Gansauge et al. (DNA. Nat. Protoc. 8 (2013), p. 737-48, p. S1-S10).*
International Search Report & Written Opinion of PCT Application No. PCT/US2017/053012, dated Mar. 29, 2018.
Bennet et al., "Coprolites, Paleogenomics and Bone Content Analysis," (2014) BioTechniques 56:289-300.
Burnham et al., "Single-stranded DNA Library Preparation Uncovers the Origin and Diversity of Ultrashort Cell-free DNA in Plasma," (2016) Scientific Reports 6(27859):1-9.
Nagalakshmi et al., "RNA-Seq: A Method for Comprehensive Transcriptome Analysis," (2010) Current Protocols in Molecular Biology 89(1):4.11.1-4.11.13.
Gansauge et al. "Single-stranded DNA Library Preparation for the Sequencing of Ancient or Damaged DNA," (2013) Nature Protocols 8(4):737-748.

\* cited by examiner

METHODS OF PREPARING AND ANALYZING CELL-FREE NUCLEIC ACID SEQUENCING LIBRARIES

CROSS REFERENCE TO RELATED APPLICATIONS

This application is a divisional of U.S. application Ser. No. 16/663,147, filed on Oct. 24, 2019, which is a divisional of U.S. application Ser. No. 15/713,296, filed on Sep. 22, 2017, which, under 35 USC § 119(e), claims priority benefit of the filing date of U.S. Provisional Patent Application No. 62/399,167, filed on Sep. 23, 2016, the disclosure of which application is herein incorporated by reference in its entirety. Under 35 USC § 119(e), this application also claims priority benefit of the filing date of U.S. Provisional Patent Application No. 62/456,029, filed on Feb. 7, 2017, the disclosure of which application is herein incorporated by reference in its entirety.

FIELD OF THE INVENTION

The present invention relates to molecular biology and bioinformatic methods, in particular, to methods for preparing and analyzing cell-free nucleic acid sequencing libraries.

BACKGROUND

Analysis of circulating cell-free DNA (cfDNA) using next generation sequencing (NGS) is recognized as a valuable tool for detection and diagnosis of cancer. Current protocols for preparing cfDNA for sequencing typically include ligation of double-stranded DNA (dsDNA) to sequencing adapters. However, a cfDNA sample typically includes other populations of DNA, such as single-stranded DNA (ssDNA) and/or damaged DNA (e.g., nicked DNA) that are not captured in a double-stranded ligation reaction. Because only the dsDNA population is captured during library preparation, precious cell-free nucleic acid material (e.g., ssDNA and/or damaged DNA) is wasted and valuable diagnostic information may be lost. There is a need for new methods of preparing a sequencing library from a cfDNA sample that captures ssDNA, dsDNA, and damaged DNA populations for sequence analysis.

SUMMARY

Aspects of the invention relate to methods for preparing and analyzing a sequencing library from a mixed cell-free DNA (cfDNA) sample, wherein the mixed sample includes double-stranded DNA (dsDNA), damaged dsDNA (e.g., nicked dsDNA), and single-stranded DNA (ssDNA) molecules. The subject methods facilitate the collection of information from dsDNA, ssDNA and damaged DNA (e.g., nicked DNA) molecules in a sample, thereby providing enhanced diagnostic information as compared to sequencing libraries that are prepared from dsDNA alone.

Aspects of the invention include a method for preparing a combined cell-free DNA (cfDNA) sequencing library from a mixed cfDNA sample, the method comprising: ligating a universal adapter comprising a unique sequence tag to at least one single-stranded DNA (ssDNA) molecule in the mixed cfDNA sample; extending the universal adapter to generate an ssDNA-derived double-stranded DNA (dsDNA) molecule; and generating a combined cfDNA sequencing library from the ssDNA-derived dsDNA molecule. In some embodiments, a method further comprises ligating a sequencing Y-adapter to the ssDNA-derived dsDNA molecule before generating the combined cfDNA sequencing library. In some embodiments, the sequencing Y-adapter comprises a unique sequence tag.

Aspects of the invention include a method for preparing a combined cfDNA sequencing library from a mixed cfDNA sample, the method comprising: ligating a first sequencing Y-adapter to a first end of a nicked dsDNA molecule in the mixed cfDNA sample, wherein the nicked dsDNA molecule comprises a nicked strand and an unnicked strand; ligating a second sequencing Y-adapter to a second end of the nicked dsDNA molecule in the mixed cfDNA sample; denaturing the sequencing Y-adapter-ligated nicked dsDNA molecule to generate a first ssDNA molecule derived from the unnicked strand, a second ssDNA molecule derived from the nicked strand, and a third ssDNA molecule derived from the nicked strand; ligating a first universal adapter comprising a unique sequence tag to the second ssDNA molecule; extending the first universal adapter to generate a first nick-derived dsDNA molecule; and generating a combined cfDNA sequencing library from the first nick-derived dsDNA molecule. In some embodiments, the first sequencing Y-adapter comprises a first unique sequence tag and the second sequencing Y-adapter comprises a second unique sequence tag. In some embodiments, the first and second unique sequence tags are the same. In some embodiments, the first and second unique sequence tags are different.

In some embodiments, a method further comprises: extending the second sequencing Y-adapter to generate a second nick-derived dsDNA molecule; ligating a third sequencing Y-adapter to the second nick-derived dsDNA molecule; and generating a combined cfDNA sequencing library from the first and the second nick-derived dsDNA molecules.

Aspects of the invention include a method for preparing a combined cfDNA sequencing library from a mixed cfDNA sample, the method comprising: ligating a first sequencing Y-adapter to a first end of a nicked dsDNA molecule in the mixed cfDNA sample, wherein the nicked dsDNA molecule comprises a nicked strand and an unnicked strand; ligating a second sequencing Y-adapter to a second end of the nicked dsDNA molecule in the mixed cfDNA sample; denaturing the sequencing Y-adapter-ligated nicked dsDNA molecule to generate a first ssDNA molecule derived from the unnicked strand, a second ssDNA molecule derived from the nicked strand, and a third ssDNA molecule derived from the nicked strand; extending the second sequencing Y-adapter to generate a first nick-derived dsDNA molecule; ligating a third sequencing Y-adapter to the first nick-derived dsDNA molecule; and generating a combined cfDNA sequencing library from the first nick-derived dsDNA molecule.

In some embodiments, the first sequencing Y-adapter comprises a first unique sequence tag, the second sequencing Y-adapter comprises a second unique sequence tag, and the third sequencing Y-adapter comprises a third unique sequence tag. In some embodiments, the first, second and third unique sequence tags are the same. In some embodiments, the first, second and third unique sequence tags are different. In some embodiments, the first and second unique sequence tags are the same, and the third unique sequence tag is different. In some embodiments, the first and third unique sequence tags are the same, and the second unique sequence tag is different. In some embodiments, the second and third unique sequence tags are the same, and the first unique sequence tag is different.

Aspects of the invention include a method for preparing a combined cfDNA sequencing library from a mixed cfDNA sample, the method comprising: extending a nicked strand of a nicked dsDNA molecule in the mixed cfDNA sample to produce a ssDNA molecule derived from the nicked strand; ligating a universal adapter comprising a unique sequence tag to the ssDNA molecule derived from the nicked strand; extending the universal adapter to generate a nicked-ssDNA-derived dsDNA molecule; and generating a combined cfDNA sequencing library from the nicked-ssDNA-derived dsDNA molecule.

In some embodiments, a method further comprises ligating a sequencing Y-adapter to the nicked-ssDNA-derived dsDNA molecule before generating the combined cfDNA sequencing library. In some embodiments, the sequencing Y-adapter comprises a unique sequence tag.

In some embodiments, a method further comprises: ligating a first sequencing Y-adapter to a first end of an intact dsDNA molecule in the mixed cfDNA sample; ligating a second sequencing Y-adapter to a second end of the intact dsDNA molecule; and generating a combined cfDNA sequencing library from the intact dsDNA molecule. In some embodiments, the first sequencing Y-adapter comprises a first unique sequence tag, and the second sequencing Y-adapter comprises a second unique sequence tag. In some embodiments, the first and the second unique sequence tags are the same. In some embodiments, the first and the second unique sequence tags are different. In some embodiments, one or more of the unique sequence tags comprises a molecular barcode sequence, a unique molecular identifier (UMI), an index sequence, a universal primer region, or any combination thereof.

In some embodiments, one or more of the universal adapters comprises an adenylated 5' end. In some embodiments, one or more of the universal adapters comprises a blocked or a phosphorylated 3' end. In some embodiments, a method further comprises performing an end repair reaction on a dsDNA molecule. In some embodiments, generating a combined cfDNA sequencing library comprises performing a PCR amplification reaction.

Aspects of the invention include a method for identifying a sequence read derived from a nicked strand of a nicked dsDNA molecule in a mixed cfDNA sample, the method comprising: generating a set of sequence reads from a combined cfDNA sequencing library, the combined sequencing library comprising: a first sequence read derived from an unnicked strand of a nicked dsDNA molecule, a second sequence read derived from a first nicked strand of a nicked dsDNA molecule, and a third sequence read derived from a second nicked strand of a nicked dsDNA molecule, wherein: the first sequence read comprises a first and a second unique sequence tag; the second sequence read comprises the first unique sequence tag and a third unique sequence tag; and the third sequence read comprises a fourth unique sequence tag and the second unique sequence tag; detecting the presence of the second sequence read comprising the first and the third unique sequence tags, or detecting the presence of the third sequence read comprising the fourth and second unique sequence tags; and identifying the second sequence read as being derived from the first nicked strand of a nicked dsDNA molecule in the mixed cfDNA sample, or identifying the third sequence read as being derived from the second nicked strand of a nicked dsDNA molecule in the mixed cfDNA sample.

In some embodiments, a method further comprises determining a fragment size of the first nicked strand of the nicked dsDNA molecule in the mixed cfDNA sample, the method further comprising: aligning the second sequence read to a reference sequence; identifying a first reference position and a second reference position on the reference sequence, wherein the first reference position aligns to a first end of the second sequence read, and wherein the second reference position aligns to a second end of the second sequence read; measuring the distance between the first reference position and the second reference position; and determining the fragment size of the first nicked strand of the nicked dsDNA molecule in the mixed cfDNA sample.

In some embodiments, a method further comprises determining a fragment size of the second nicked strand of the nicked dsDNA molecule in the mixed cfDNA sample, the method further comprising: aligning the third sequence read to a reference sequence; identifying a first reference position and a second reference position on the reference sequence, wherein the first reference position aligns to a first end of the third sequence read, and wherein the second reference position aligns to a second end of the third sequence read; measuring the distance between the first reference position and the second reference position; and determining the fragment size of the second nicked strand of the nicked dsDNA molecule in the mixed cfDNA sample.

In some embodiments, a method further comprises determining a genome position of the first nicked strand of the nicked dsDNA molecule in the mixed cfDNA sample, the method further comprising: aligning the second sequence read to a reference genome; identifying a first reference position, wherein the first reference position aligns to a first end of the second sequence read; and/or identifying a second reference position, wherein the second reference position aligns to a second end of the second sequence read; identifying a start position of the first nicked strand of the nicked dsDNA molecule based on the first reference position, and/or identifying a stop position of the first nicked strand of the nicked dsDNA molecule based on the second reference position; and determining the genome position of the second nicked strand of the nicked dsDNA molecule based on the identified start position and/or the identified stop position.

In some embodiments, a method further comprises determining a genome position of the second nicked strand of the nicked dsDNA molecule in the mixed cfDNA sample, the method further comprising: aligning the third sequence read to a reference genome; identifying a first reference position, wherein the first reference position aligns to a first end of the third sequence read, and/or identifying a second reference position, wherein the second reference position aligns to a second end of the third sequence read; identifying a start position of the second nicked strand of the nicked dsDNA molecule based on the first reference position, and/or identifying a stop position of the second nicked strand of the nicked dsDNA molecule based on the second reference position; and determining the genome position of the second nicked strand of the nicked dsDNA molecule based on the identified start position and/or the identified stop position.

Aspects of the invention include a method for determining a quantity of sequence reads derived from an ssDNA molecule, a nicked strand of a nicked dsDNA molecule, an intact dsDNA molecule, and/or an unnicked strand of a nicked dsDNA molecule in a mixed cfDNA sample, the method comprising: generating a set of sequence reads from a combined cfDNA sequencing library, the combined cfDNA sequencing library comprising: one or more first sequence reads derived from an unnicked strand of a nicked dsDNA molecule; one or more second sequence reads derived from a first nicked strand of a nicked dsDNA molecule; one or more third sequence reads derived from an unnicked strand of a nicked dsDNA molecule; and one or more fourth sequence reads derived from a ssDNA molecule, wherein:

the one or more first sequence reads comprise a first and a second unique sequence tag; the one or more second sequence reads comprise the first unique sequence tag and a third unique sequence tag; the one or more third sequence reads comprise a fourth and the second unique sequence tags; and the one or more fourth sequence reads comprises a fifth unique sequence tag and a sixth unique sequence tag; detecting the one or more first, second, third, and/or fourth sequence reads based on the unique sequence tags; and quantifying a number of first, second, third, and/or fourth sequence reads to determine the quantity of sequence reads derived from the ssDNA molecule, the nicked strand of the nicked dsDNA molecule, the intact dsDNA molecule, and/or the unnicked strand of the nicked dsDNA molecule in the mixed cfDNA sample. In some embodiments, the mixed cfDNA sample is isolated from a plasma fraction of a blood sample.

DEFINITIONS

Figure 1:
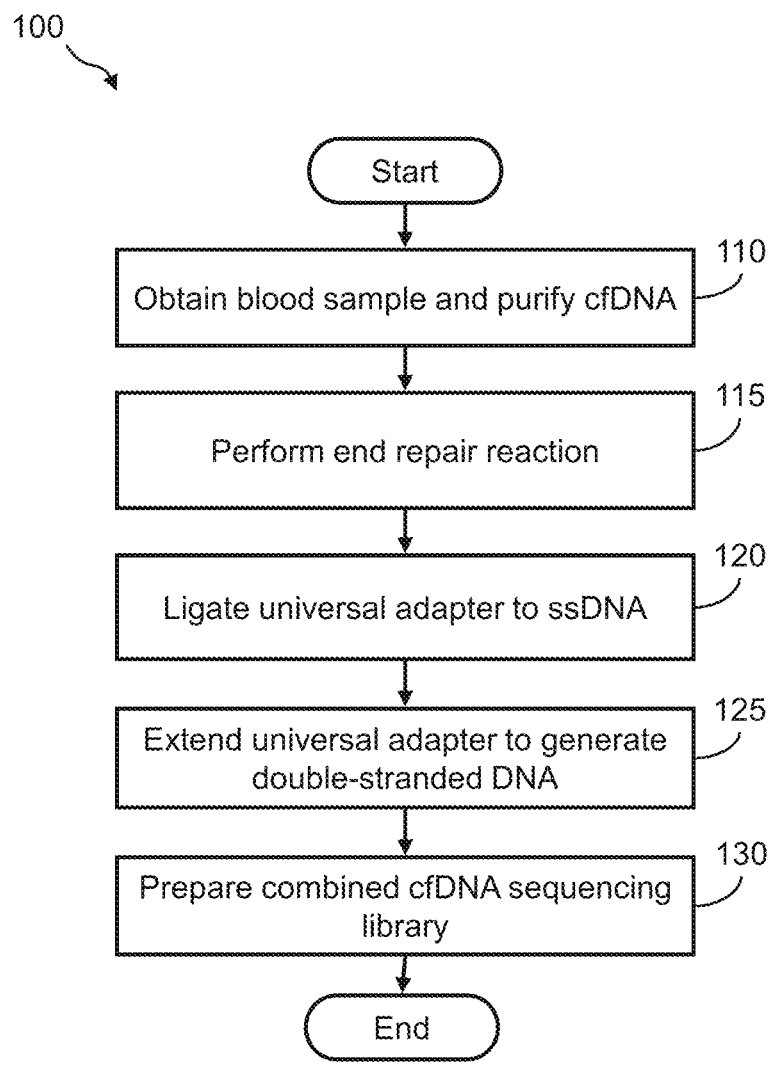
FIG. 1 is a flow diagram that illustrates the steps of a method for preparing a sequencing library from a mixed cfDNA sample, wherein ssDNA molecules in a mixture of dsDNA and ssDNA molecules are tagged with a single-strand specific sequence (e.g., a barcode sequence) and converted to dsDNA prior to preparation of a combined cfDNA library for sequencing.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, NY 1994), provides one skilled in the art with a general guide to many of the terms used in the present application, as do the following, each of which is incorporated by reference herein in its entirety: Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, $6^{th}$ edition (Saunders, 2007).

All publications mentioned herein are expressly incorporated herein by reference to disclose and describe the methods and/or materials in connection with which the publications are cited.

The term "amplicon" as used herein means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase, or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references, each of which are incorporated herein by reference herein in their entirety: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g., "real-time PCR", or "real-time NASBA" as described in Leone et al, Nucleic Acids Research, 26: 2150-2155 (1998), and like references.

As used herein, the term "amplifying" means performing an amplification reaction. A "reaction mixture" means a solution containing all the necessary reactants for performing a reaction, which may include, but is not be limited to, buffering agents to maintain pH at a selected level during a reaction, salts, co-factors, scavengers, and the like.

The terms "fragment" or "segment", as used interchangeably herein, refer to a portion of a larger polynucleotide molecule. A polynucleotide, for example, can be broken up, or fragmented into, a plurality of segments. Various methods of fragmenting nucleic acid are well known in the art. These methods may be, for example, either chemical or physical or enzymatic in nature. Enzymatic fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave a polynucleotide at known or unknown locations. Physical fragmentation methods may involve subjecting a polynucleotide to a high shear rate. High shear rates may be produced, for example, by moving DNA through a chamber or channel with pits or spikes, or forcing a DNA sample through a restricted size flow passage, e.g., an aperture having a cross sectional dimension in the micron or submicron range. Other physical methods include sonication and nebulization. Combinations of physical and chemical fragmentation methods may likewise be employed, such as fragmentation by heat and ion-mediated hydrolysis. See, e.g., Sambrook et al., "Molecular Cloning: A Laboratory Manual," 3rd Ed. Cold Spring Harbor Laboratory Press, Cold Spring Harbor, N.Y. (2001) ("Sambrook et al.) which is incorporated herein by reference for all purposes. These methods can be optimized to digest a nucleic acid into fragments of a selected size range.

The terms "polymerase chain reaction" or "PCR", as used interchangeably herein, mean a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors that are well-known to those of ordinary skill in the art, e.g., exemplified by the following references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including, but not limited to, RT-PCR, real-time PCR, nested PCR, quantitative PCR, multiplexed PCR, and the like. The particular format of PCR being employed is discernible by one skilled in the art from the context of an application. Reaction volumes can range from a few hundred nanoliters, e.g., 200 nL, to a few hundred µL, e.g., 200 µL. "Reverse transcription PCR," or "RT-PCR," means a PCR that is preceded by a reverse transcription reaction that converts a target RNA to a complementary single stranded DNA, which is then amplified, an example of which is described in Tecott et al, U.S. Pat. No. 5,168,038, the disclosure of which is incorporated herein by reference in its entirety. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); the disclosures of which are hereby incorporated by reference herein in their entireties. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Asymmetric PCR" means a PCR wherein one of the two primers employed is in great excess concentration so that the reaction is primarily a linear amplification in which one of the two strands of a target nucleic acid is preferentially copied. The excess concentration of asymmetric PCR primers may be expressed as a concentration ratio. Typical ratios are in the range of from 10 to 100. "Multiplexed PCR" means a PCR wherein multiple target sequences (or a single target sequence and one or more reference sequences) are simultaneously carried out in the same reaction mixture, e.g., Bernard et al, Anal. Biochem., 273: 221-228 (1999)(two-color real-time PCR). Usually, distinct sets of primers are employed for each sequence being amplified. Typically, the number of target sequences in a multiplex PCR is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references, which are incorporated by reference herein in their entireties: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); and Becker-Andre et al, Nucleic Acids Research, 17: 9437-9446 (1989).

The term "primer" as used herein means an oligonucleotide, either natural or synthetic, that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually, primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following reference that is incorporated by reference herein in its entirety: Dieffenbach, editor, PCR Primer: A Laboratory Manual, 2$^{nd}$ Edition (Cold Spring Harbor Press, New York, 2003).

The terms "unique sequence tag", "sequence tag", "tag" or "barcode", as used interchangeably herein, refer to an oligonucleotide that is attached to a polynucleotide or template molecule and is used to identify and/or track the polynucleotide or template in a reaction or a series of reactions. A sequence tag may be attached to the 3'- or 5'-end of a polynucleotide or template, or it may be inserted into the interior of such polynucleotide or template to form a linear conjugate, sometimes referred to herein as a "tagged polynucleotide," or "tagged template," or the like. Sequence tags may vary widely in size and compositions; the following references, which are incorporated herein by reference in their entireties, provide guidance for selecting sets of sequence tags appropriate for particular embodiments: Brenner, U.S. Pat. No. 5,635,400; Brenner and Macevicz, U.S. Pat. No. 7,537,897; Brenner et al, Proc. Natl. Acad. Sci., 97: 1665-1670 (2000); Church et al, European patent publication 0 303 459; Shoemaker et al, Nature Genetics, 14: 450-456 (1996); Morris et al, European patent publication 0799897A1; Wallace, U.S. Pat. No. 5,981,179; and the like. Lengths and compositions of sequence tags can vary widely, and the selection of particular lengths and/or compositions depends on several factors including, without limitation, how tags are used to generate a readout, e.g., via a hybridization reaction or via an enzymatic reaction, such as sequencing; whether they are labeled, e.g., with a fluorescent dye or the like; the number of distinguishable oligonucleotide tags required to unambiguously identify a set of polynucleotides, and the like, and how different the tags of a particular set must be in order to ensure reliable identification, e.g., freedom from cross hybridization or misidentification from sequencing errors. In one aspect, sequence tags can each have a length within a range of from about 2 to about 36 nucleotides, or from about 4 to about 30 nucleotides, or from about 8 to about 20 nucleotides, or from about 6 to about 10 nucleotides. In one aspect, sets of sequence tags are used, wherein each sequence tag of a set has a unique nucleotide sequence that differs from that of every other tag of the same set by at least two bases; in another aspect, sets of sequence tags are used wherein the sequence of each tag of a set differs from that of every other tag of the same set by at least three bases.

DETAILED DESCRIPTION

Aspects of the invention relate to methods for preparing and analyzing a sequencing library from a mixed cell-free DNA (cfDNA) sample, wherein the mixed sample includes double-stranded DNA (dsDNA), damaged dsDNA (e.g., nicked dsDNA), and single-stranded DNA (ssDNA) molecules. The subject methods facilitate the collection of information from dsDNA, ssDNA and damaged DNA (e.g., nicked DNA) molecules in a sample, thereby providing enhanced diagnostic information as compared to sequencing libraries that are prepared from dsDNA alone.

In some embodiments, the methods of the invention involve differential tagging of populations of cfDNA molecules (e.g., dsDNA molecules, ssDNA molecules, and nicked dsDNA molecules) in a sample with unique sequence tags to distinguish sequence information derived from one population of cfDNA molecules (e.g., dsDNA molecules) from sequence information derived from another population of cfDNA molecules (e.g., ssDNA molecules). Analysis of all populations of cfDNA molecules (e.g., dsDNA molecules, ssDNA molecules, and nicked dsDNA molecules) may increase the sensitivity of certain protocols, for example, a cancer screening protocol. Without being bound by theory, it is believed that ssDNA molecules and/or nicked dsDNA may provide additional valuable insight for cancer detection and screening from a cfDNA sample, and/or may be more representative of tumor content in a cfDNA sample.

Aspects of the invention involve the use of unique sequence tags. Unique sequence tags in accordance with embodiments of the invention can serve many functions. For example, unique sequence tags can include molecular barcode sequences, unique molecular identifier (UMI) sequences, or index sequences. In one embodiment, unique sequence tags (e.g., barcode or index sequences) can be used to identify DNA sequences originating from a common source such as a sample type, tissue, patient, or individual. In accordance with one embodiment, barcodes or index sequences can be used for multiplex sequencing. In one embodiment, unique sequence tags (e.g., unique molecular identifiers (UMIs)) can be used to identify unique nucleic acid sequences from a mixed cfDNA sample. For example, differing unique sequence tags (e.g., UMIs) can be used to differentiate ssDNA molecules, dsDNA molecules, or damaged molecules (e.g., nicked dsDNA) contained in a cfDNA sample. In another embodiment, unique sequence tags (e.g., UMIs) can be used to reduce amplification bias, which is the asymmetric amplification of different targets due to differences in nucleic acid composition (e.g., high GC content). The unique sequence tags (UMIs) can be used to discriminate between nucleic acid mutations that arise during amplification. The unique sequence tags can be present in a multi-functional nucleic acid adapter, which adapter can comprise both a unique sequence tag and a universal priming site. In some embodiments, unique sequence tags can be greater than about 5, 6, 7, 8, 9, 10, 11, 12, 13, 14, 15, 16, 17, or 18 nucleic acids in length.

In one embodiment, ssDNA molecules in a mixture of dsDNA and ssDNA molecules can be tagged with a unique sequence tags (e.g., ssDNA-specific tags, barcodes or UMIs) using an ssDNA ligation protocol and converted to dsDNA prior to preparation of a combined cfDNA library.

In another embodiment, dsDNA molecules in a mixture of dsDNA and ssDNA molecules can be tagged with unique sequence tags (e.g., UMIs) in a dsDNA ligation protocol using Y-shaped sequencing adapters and then ssDNA molecules can be tagged with a unique sequence tags (e.g., barcode or unique UMI) and converted to dsDNA.

In one embodiment, the incorporated unique sequences tags and ssDNA-specific tag can be used to distinguish sequencing reads as being originally derived from dsDNA or ssDNA in a cfDNA sample.

In another embodiment, the incorporated unique sequences tags (e.g., UMIs) and ssDNA-specific tags (e.g., barcodes or UMIs) can be used to obtain fragment size information and genome position associated with sequencing reads from nicked dsDNA fragments in a cfDNA sample.

In yet another embodiment, the incorporated unique sequences tags (e.g., UMIs) and ssDNA-specific tags (e.g., barcodes or UMIs) are used to reduce error introduced by amplification, library preparation, and/or sequencing.

Methods of Preparing a Combined cfDNA Sequencing Library

Aspects of the invention relate to methods for preparing combined cfDNA sequencing libraries that include sequencing information from dsDNA, ssDNA and/or damaged DNA (e.g., nicked DNA). Once prepared, a combined cfDNA sequencing library can be used to determine, e.g., the presence of a genetic marker or interest, such as, e.g., a genetic mutation associated with a known type of cancer. As such, the present methods are useful in conjunction with methods of determining the presence of (e.g., diagnosing a subject with) a disease or disorder that is associated with the presence of a genetic marker (e.g., a hyperproliferative disorder, such as a cancer).

FIG. 1 is a flow diagram illustrating a method 100 for preparing a sequencing library from a mixed cfDNA sample comprising dsDNA, damaged dsDNA (e.g., nicked dsDNA), and ssDNA molecules in accordance with one embodiment of the present invention. Method 100 includes, but is not limited to, the following steps.

In step 110, a blood sample is obtained and circulating cfDNA is isolated from the plasma fraction. The isolated cfDNA sample includes a mixture of dsDNA and ssDNA molecules. The dsDNA population may include molecules with overhanging ends, gaps, and/or single strand nicks.

In step 115, an end repair reaction is performed to repair any overhanging ends and gaps in the dsDNA population.

In step 120, a universal adapter is ligated to the 3'-OH ends of the ssDNA molecules. For example, a universal adapter is added to the 3'-OH end of a ssDNA molecule using a ssDNA ligation reaction. The universal adapter may include a single-strand specific tag sequence (e.g., a barcode or UMI) and/or a universal primer sequence (e.g., an SBS primer sequence). In one embodiment, the single-strand specific tag (e.g., barcode sequence or UMI) can be used during data analysis to identify and classify sequencing reads as being originally derived from ssDNA molecules in the isolated cfDNA sample as described in more detail with reference to FIGS. 6A and 6B. In one embodiment, the universal adapter may also include a unique molecular identifier (UMI) which can be used to reduce error introduced by amplification, library preparation, and sequencing.

In general, any known ligase can be used for ligation of the universal adapter to the ssDNA molecules. In one embodiment, an ssDNA ligation reaction uses Thermostable 5' AppDNA/RNA ligase (available from New England Bio-Labs (Ipswich, Mass.)) for ligation of a universal adapter to a 3'-OH end of an ssDNA molecule. In another example, an ssDNA ligation reaction uses CircLigase II (Epicentre) for ligation of a universal adapter to a 3'-OH end of an ssDNA molecule. In accordance with this embodiment, a universal adapter can be adenylated at the 5'-end and blocked or phosphorylated at the 3'-end.

In step 125, adapter ligated ssDNA molecules are converted to dsDNA in an extension reaction. For example, an extension primer can be used that includes a primer sequence complementary to a universal adapter for polymerase-based extension to form dsDNA (e.g., using polymerase chain reaction (PCR)).

In step 130, a combined cfDNA sequencing library is prepared. For example, a standard sequencing library preparation protocol (e.g., TRUSEQ® library preparation protocol (Illumina, Inc.)) that includes the steps of end repair, 3' end A-tailing, ligation of sequencing Y-adapters that include a unique molecular identifier (UMI) sequence, and PCR amplification can be used to complete preparation of the combined sequencing library from the mixed cfDNA sample. The sequencing library now includes amplicons derived from ssDNA molecules that are tagged with a single-strand specific sequence tag (e.g., barcode) and a pair of UMI sequences, as well as amplicons derived from dsDNA molecules that are tagged with unique sequences tags. Use of a single-strand specific sequence tag allows for subsequent identification of sequences that originated from ssDNA molecules in the cfDNA sample, whereas use of UMI sequence tags for the dsDNA molecules allows for subsequent identification of sequences that originated from dsDNA molecules in the cfDNA sample. In some embodiments, the dsDNA can be tagged with a first unique sequence tag for the forward strand and a second unique sequence tag for the reverse strand.

Figure 2:
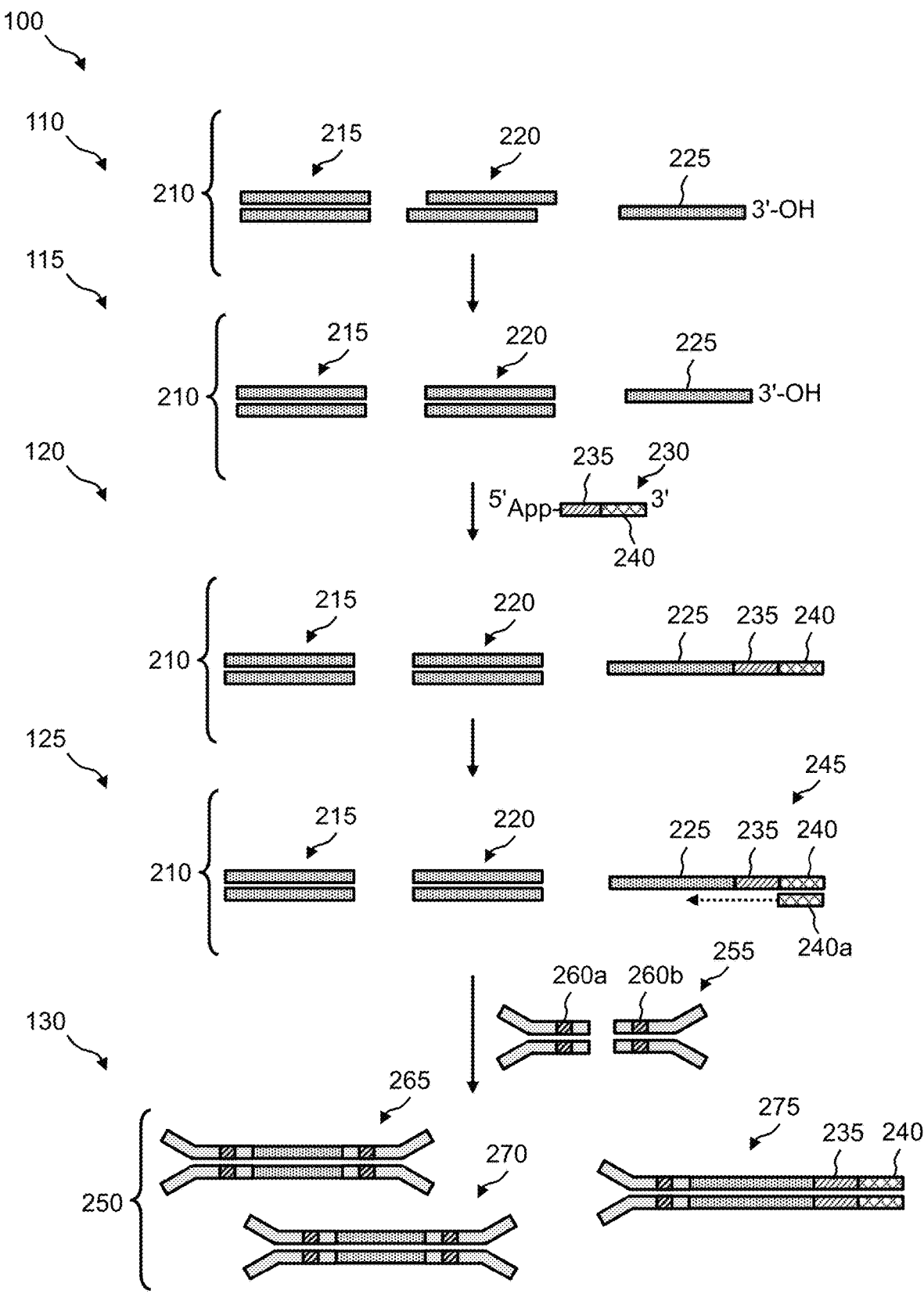
FIG. 2 shows pictorially the steps of the method of FIG. 1.

FIG. 2 shows pictorially the steps of method 100 of FIG. 1. Namely, at step 110, a blood sample is obtained and circulating cfDNA is isolated from the plasma fraction (not shown). An isolated cfDNA sample 210 includes, for example, a mixture of dsDNA molecules 215, dsDNA molecules with a free 3' or 5' end overhang 220, and ssDNA molecules 225. In one embodiment, the isolated cfDNA sample may also include nicked dsDNA molecules (not shown).

At step 115, an end repair reaction is performed to repair overhanging ends in dsDNA molecule 220. In one embodiment, step 115 may also include a step for extending a nicked strand of nicked dsDNA molecules (not shown). This nick extension, which can be carried out for example using Phi29 5'-displacing DNA polymerase, would extend the nicked strand, forming a blunt end dsDNA molecule, and would release an ssDNA molecule. The released ssDNA molecule can be captured in accordance with subsequent processing steps, and quantified.

At step 120, a universal adapter 230 is ligated to the 3'-OH ends of ssDNA molecule 225. For example, universal adapter 230 is added to the 3'-OH end of ssDNA molecule 225 using an ssDNA ligation reaction. Universal adapter 230 may include a single-strand specific tag (e.g., a barcode region) 235 and a universal primer region 240 (e.g., an SBS primer sequence) and a UMI sequence.

At step 125, adapter ligated ssDNA molecule 225 is converted to double-stranded DNA in an extension reaction. For example, an extension primer 240a that includes a primer region complementary to universal primer region 240 in universal adapter 230 is used in a primer extension reaction to form dsDNA. In one embodiment, the extension primer 240a is blocked on the 5' end. After primer extension, the sample 210 includes a mixture of dsDNA molecule 215, repaired dsDNA molecule 220, and a tagged dsDNA molecule 245 derived from the ssDNA molecules 225 in the original cfDNA sample.

At step 130, a combined cfDNA sequencing library 250 is prepared. For example, a standard sequencing library preparation protocol (e.g., TRUSEQ® library preparation protocol (Illumina, Inc.)) that includes the steps of end repair (not shown), 3' end A-tailing (not shown), ligation of Y-adapters 255, and PCR amplification (not shown) can be used to complete preparation of the combined sequencing library 250. Y-adapters 255 may include first and second unique sequence tags 260a and 260b (e.g., a pair of unique molecular identifier (UMI) sequences). In accordance with this embodiment, Y-adapters 255 are ligated to dsDNA fragments in a double-strand DNA ligation reaction. In one embodiment, the first and second unique sequence tags 260a and 260b (e.g., UMIs) can be used during data analysis to classify sequencing reads as derived from dsDNA molecules in the isolated cfDNA sample, as described in more detail with reference to FIGS. 5A and 5B. In another embodiment, the first and second unique sequence tags 260a and 260b (e.g., UMIs) can be used during data analysis to determine fragment size information and genomic position of nicks in a dsDNA fragment as described in more detail with reference to FIGS. 6A and 6B. In accordance with this embodiment, third and fourth unique sequence tags may be ligated to the 3' and 5' ends of the dsDNA nick (not shown). In another embodiment, UMI regions 260a and 260b can be used to reduce error introduced by amplification, library preparation, and sequencing.

Sequencing library 250 includes amplicon 265 derived from dsDNA 215, amplicon 270 derived from repaired dsDNA 220, and amplicon 275 derived from ssDNA 225. DNA amplicons 265 and 270, which originated from dsDNA molecules in the original cfDNA sample, include a first unique sequence tag 260a and a second unique sequence tag 260b that can be used for subsequent identification and classification. Likewise, amplicon 275 includes a single-strand specific tag 235 that can be used for identification and classification of sequences originating from ssDNA molecules in the original cfDNA sample.

In some embodiments, dsDNA molecules 215 can be cleaved using an endonuclease specific for sites where the dsDNA is nicked (e.g., using EndoTT) prior to step 115 of method 100 of FIG. 1. The use of an endonuclease to cleave a nicked dsDNA molecule at the nick site generates shorter dsDNA molecules. These shorter dsDNA molecules can be captured in subsequent library preparation steps, in accordance with the processing steps detailed herein, and quantified, providing valuable information about the damaged or nicked dsDNA molecules in the original cfDNA sample. In an alternative embodiment, nicks in the dsDNA molecules 215 can be repaired prior to cleaving with the site specific endonuclease, as detailed elsewhere herein.

Figure 3:
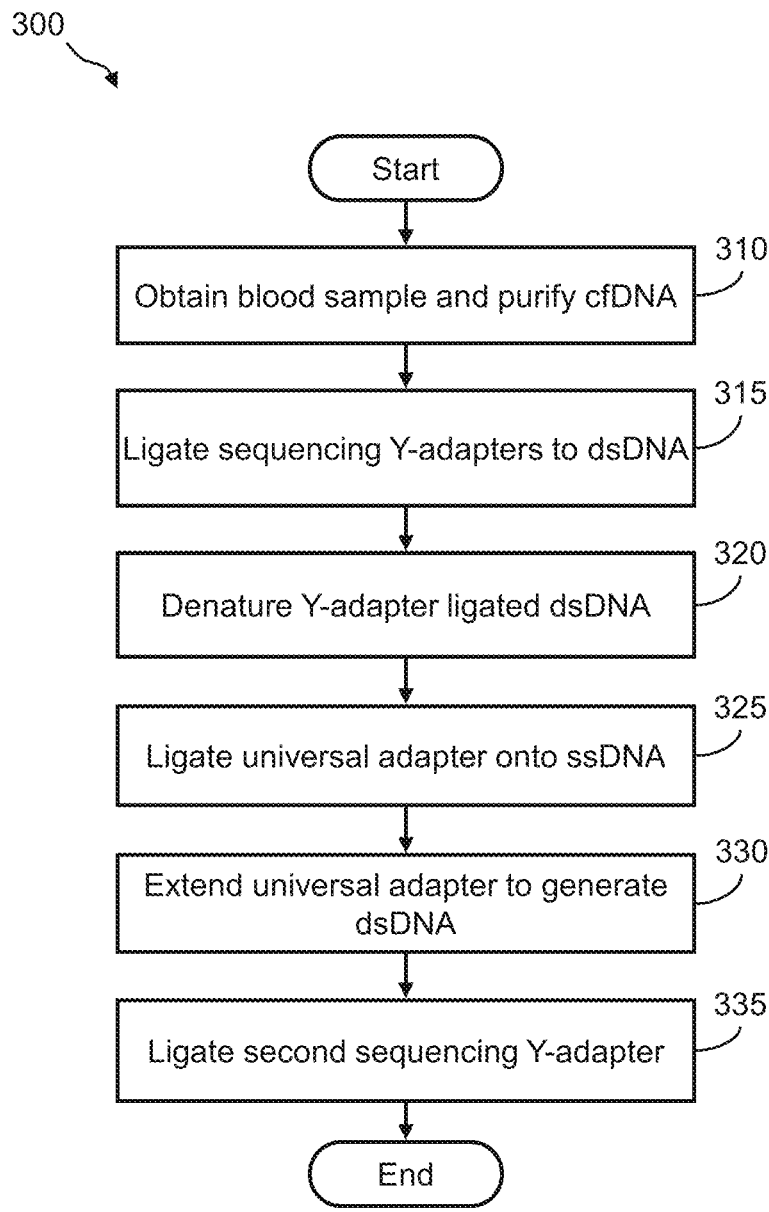
FIG. 3 is a flow diagram that illustrates the steps of a method for preparing a sequencing library from a mixed cfDNA sample, wherein sequencing Y-adapters that include unique sequence tags (e.g., unique molecular identifiers (UMIs)) are ligated onto dsDNA molecules in a mixture of dsDNA and ssDNA molecules prior to denaturing dsDNA and subsequent extension of ssDNA molecules to dsDNA amplicons.

FIG. 3 is a flow diagram illustrating a method 300 for preparing a sequencing library from a mixed cfDNA sample comprising dsDNA, damaged dsDNA (e.g., nicked dsDNA), and ssDNA molecules in accordance with one embodiment of the invention. In this approach, nicked dsDNA fragments can be converted into sequence amplicons while maintaining fragment size information. Method 300 includes, but is not limited to, the following steps.

In step 310, a biological sample is obtained (e.g., a blood sample) and circulating cfDNA is isolated from the plasma fraction. The isolated cfDNA includes a mixture of dsDNA and ssDNA molecules. The dsDNA population includes, for example, molecules with single strand nicks.

In step 315, sequencing Y-adapters that include unique sequence tags (e.g., UMIs) are ligated onto the dsDNA molecules. For example, a standard sequencing library preparation protocol (e.g., TRUSEQ® library preparation protocol (Illumina, Inc.)) that includes the steps of end repair, 3' end A-tailing, ligation of sequencing Y-adapters, and PCR amplification can be used to prepare Y-adapter ligated dsDNA. In one embodiment, the unique sequence tags (UMIs) in the Y-adapters can be used during sequence data analysis to obtain fragment size information and genomic position of nicks in a dsDNA fragment as described in more detail with reference to FIGS. 6A and 6B. In another embodiment, UMI regions 260a and 260b are used to reduce error introduced by amplification, library preparation, and sequencing.

In step 320, Y-adapter ligated dsDNA molecules are denatured. Any known method for denaturing dsDNA to obtain ssDNA molecules can be used. For example, the dsDNA molecules can be denatured using heat.

In step 325, a universal adapter is ligated to the 3'-OH ends of ssDNA molecules originating from the cfDNA sample and to ssDNA molecules derived from denatured, nicked dsDNA. For example, a universal adapter is added to the 3'-OH end of the ssDNA molecules using a ligation reaction. The universal adapter may include a unique sequence tag (e.g., a barcode, UMI or index sequence) and a universal primer sequence (e.g., an SBS primer sequence). The unique sequence tag can be used during data analysis to identify and classify sequencing reads as being originally derived from nicked dsDNA molecules in the isolated cfDNA sample, as described in more detail with reference to FIGS. 6A and 6B.

In general, any known ligase can be used for ligation of a universal adapter to an ssDNA molecule. In one example, the ligation reaction uses Thermostable 5' AppDNA/RNA ligase (available from New England BioLabs (Ipswich, Mass.)) for ligation of a universal adapter to an ssDNA molecule. In another example, the ligation reaction uses CircLigase II (Epicentre) for ligation of a universal adapter to an ssDNA molecule. In accordance with one embodiment, a universal adapter may be adenylated at the 5'-end and blocked or phosphorylated at the 3'-end.

In step 330, adapter ligated ssDNA molecules are converted to dsDNA in an extension reaction. In one embodiment, an extension primer can be used that includes a primer sequence complementary to the universal adapter for polymerase based extension to form dsDNA (e.g., using polymerase chain reaction (PCR)). For example, an extension primer that includes a primer sequence that is complementary to the universal primer sequence in the universal adapter is used in a primer extension reaction to form dsDNA. Similarly, an extension primer that includes a primer sequence complementary to the Y-shaped sequencing adapter can be used for polymerase based extension to form dsDNA (e.g., using PCR).

In step 335, a second Y-shaped sequencing adapter can be ligated onto the newly synthesized dsDNA.

Figure 4A:
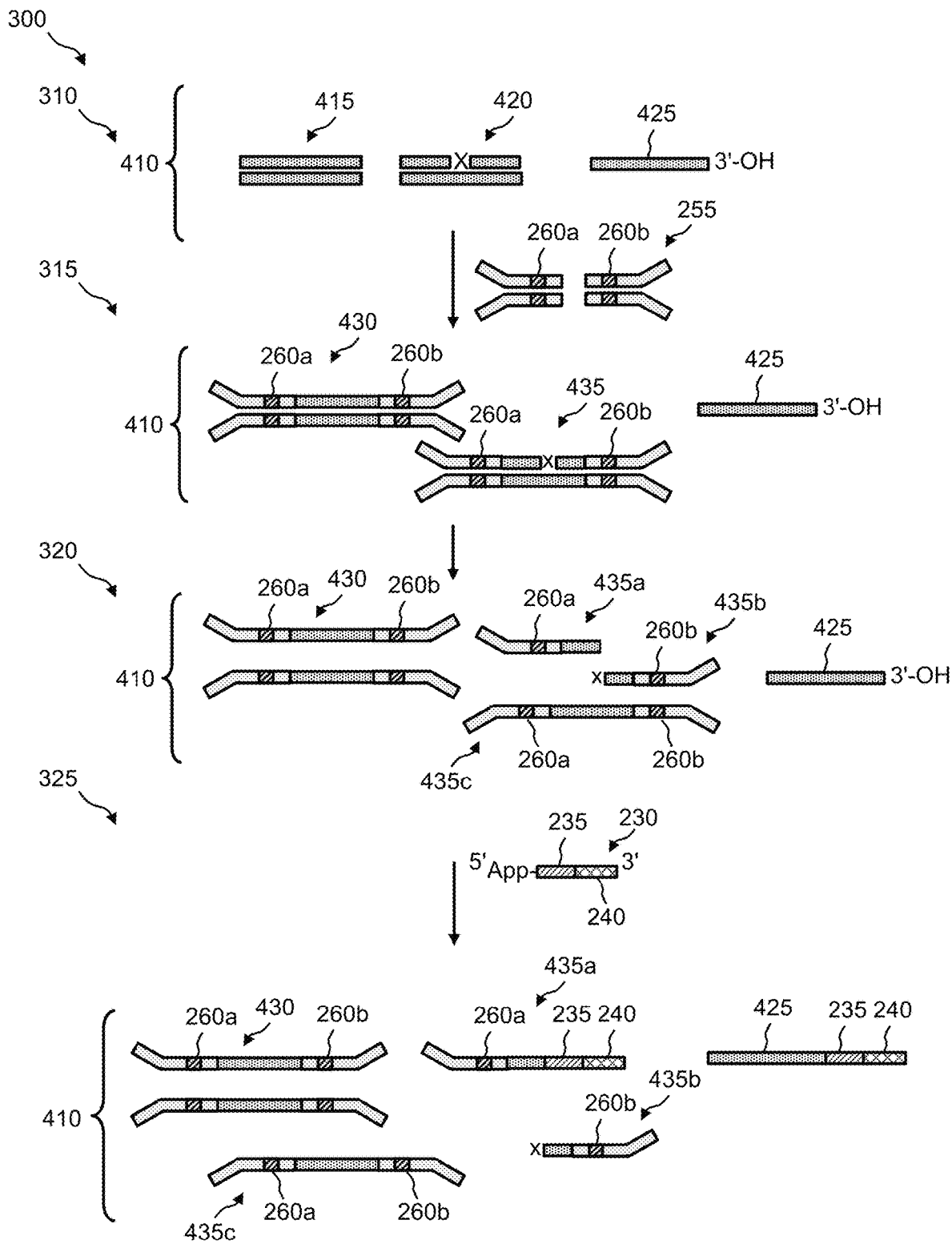
FIGS. 4A and 4B show pictorially the steps of the method of FIG. 3.
Figure 4B:
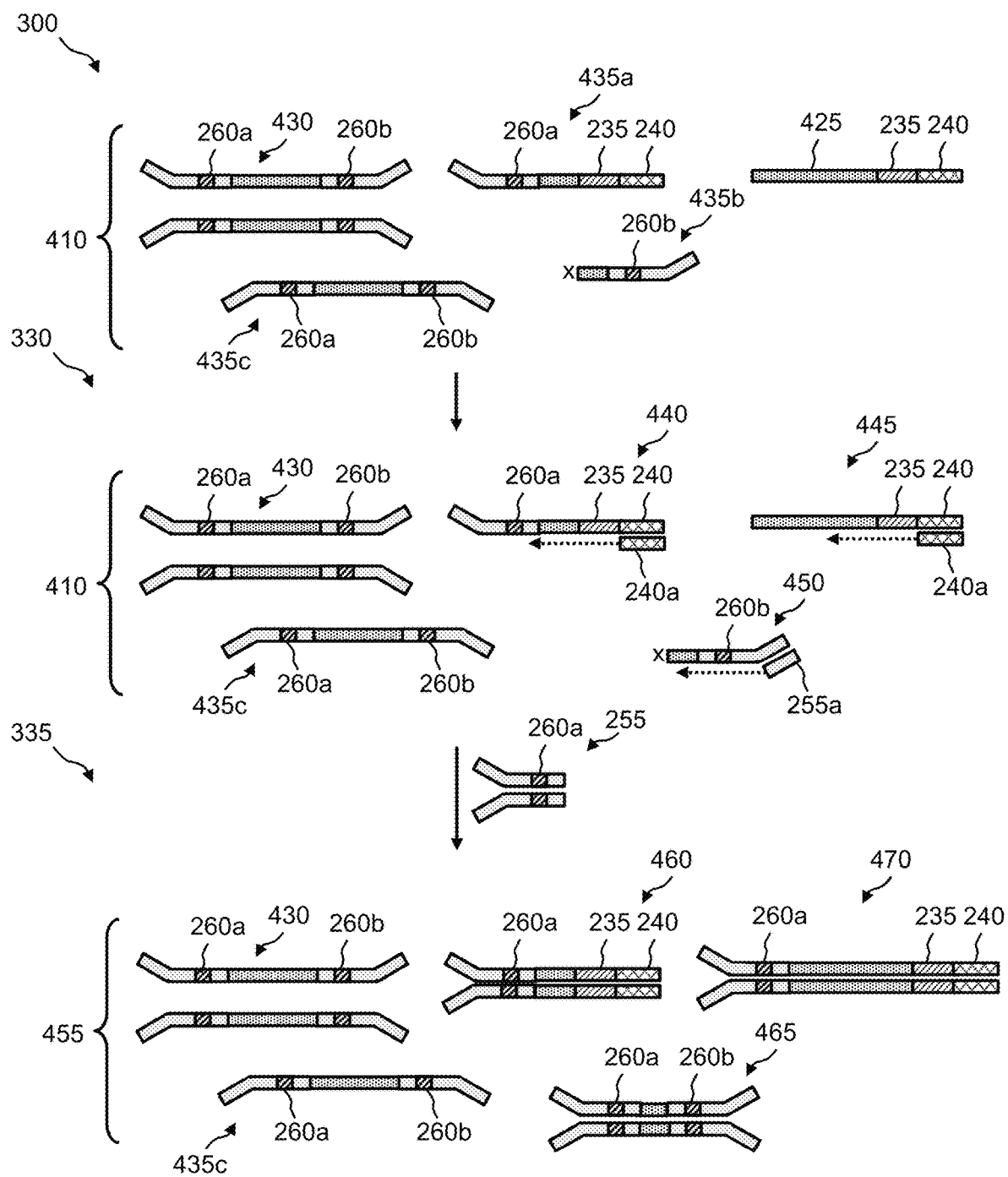

FIGS. 4A and 4B show pictorially the steps of method 300 of FIG. 3. Namely, at step 310, a biological sample (e.g., a blood sample) is obtained and circulating cfDNA is isolated from the plasma fraction (not shown). An isolated cfDNA sample 410 includes a mixture of dsDNA molecules 415, nicked dsDNA molecules 420, and ssDNA molecules 425.

At step 315, Y-shaped sequencing adapters 255 are ligated onto dsDNA molecules 415 and 420. In one embodiment, the single-strand 3' and 5' arms of the Y-adapter can be blocked. For example, a standard sequencing library preparation protocol (e.g., TRUSEQ® library preparation protocol (Illumina, Inc.)) that includes the steps of end repair (not shown), 3' end A-tailing (not shown), ligation of sequencing adapters, and PCR amplification (not shown) may be used to prepare Y-adapter ligated dsDNA molecules 430 and 435. In one embodiment, the Y-adapters include unique sequence tags (UMIs) that can be used to identify individual strands of a dsDNA molecule.

At step 320, Y-adapter ligated dsDNA molecules 430 and 435 are denatured. Because Y-adapter ligated dsDNA molecule 435 includes a nick (indicated by "x"), two ssDNA molecules 435a and 435b and an intact ssDNA molecule 435c are formed.

At step 325, a universal adapter 230 is ligated to the 3'-OH ends of ssDNA molecule 425 and to the ssDNA molecule 435a derived from the denatured, nicked dsDNA molecule 420. For example, universal adapter 230 is added to the 3'-OH end of ssDNA molecules 425 and 435a using an ssDNA ligation reaction. Universal adapter 230 may include a unique sequence tag (e.g., a barcode region or UMI sequence) 235 and universal primer region 240 (e.g., an SBS primer sequence).

At step 330, adapter ligated ssDNA molecules 425, 435a, and 435b are converted to double-stranded DNA in a primer extension reaction (e.g., PCR) resulting in blunt end dsDNA molecules. For example, an extension primer 240a that includes a primer region that is complementary to universal primer region 240 in universal adapter 230 is used in a primer extension reaction to form dsDNA molecule 440 derived from ssDNA molecules 435a and dsDNA molecules 445 derived from adapter-ligated ssDNA molecule 425. In one embodiment, the 5' end of primer 240a is blocked. Similarly, an extension primer that includes a primer region 255a that is complementary to Y-shaped sequencing adapter 255 is used in a primer extension reaction to form dsDNA molecule 450 derived from ssDNA molecule 435b. In one embodiment, the 5' end of primer 255a is blocked.

At step 335, 5' Y-shaped sequencing adapters 255 are ligated onto the newly synthesized dsDNA molecules 440, 445, and 450. A sequencing library 455 includes amplicon 430 derived from dsDNA molecule 415, amplicon 435c derived from the intact strand of nicked dsDNA molecule 420, amplicons 460 and 465 derived from nicked dsDNA molecule 420, and amplicon 470 derived from ssDNA molecule 425. Amplicons 430, 435c, and 465 include unique sequence tags (UMIs) 260a and 260b, and amplicons 460 and 470 include unique sequence tags 260a and a unique single-stranded specific sequence tag 235. In one embodiment, the unique sequence tags (UMIs) 260a and 260b differ than the unique sequence tags (UMIs) used in step 315. Use of single-strand specific sequence tags allows for subsequent identification of sequences that originated from ssDNA molecules in the cfDNA sample, whereas use of a unique sequence tags (UMIs) on the dsDNA molecules allows for subsequent identification of sequences that originated from dsDNA molecules in the cfDNA sample. In some embodiments, the dsDNA can be tagged with a first unique specific tag for the forward strand and a second unique sequence tag for the reverse strand.

Sequencing and Bioinformatics

Aspects of the invention include sequencing of nucleic acid molecules to generate a plurality of sequence reads, compilation of a plurality of sequence reads into a sequencing library, and bioinformatic manipulation of the sequence reads and/or sequencing library to determine whether a given sequence read originated from an ssDNA, dsDNA, and/or damaged DNA population in the biological sample. In some embodiments, one or more aspects of the subject methods are conducted using a suitably-programmed computer system, as described further herein.

In certain embodiments, a sample is collected from a subject, followed by enrichment for genetic regions or genetic fragments of interest. For example, in some embodiments, a sample can be enriched by hybridization to a nucleotide array comprising cancer-related genes or gene fragments of interest. In some embodiments, a sample can be enriched for genes of interest (e.g., cancer-associated genes) using other methods known in the art, such as hybrid capture. See, e.g., Lapidus (U.S. Pat. No. 7,666,593), the contents of which is incorporated by reference herein in its entirety. In one hybrid capture method, a solution-based hybridization method is used that includes the use of biotinylated oligonucleotides and streptavidin coated magnetic beads. See, e.g., Duncavage et al., J Mol Diagn. 13(3): 325-333 (2011); and Newman et al., Nat Med. 20(5): 548-554 (2014). Isolation of nucleic acid from a sample in accordance with the methods of the invention can be done according to any method known in the art.

Sequencing may be by any method or combination of methods known in the art. For example, known DNA sequencing techniques include, but are not limited to, classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, Polony sequencing, and SOLiD sequencing. Sequencing of separated molecules has more recently been demonstrated by sequential or single extension reactions using polymerases or ligases as well as by single or sequential differential hybridizations with libraries of probes.

One conventional method to perform sequencing is by chain termination and gel separation, as described by Sanger et al., Proc Natl. Acad. Sci. USA, 74(12): 5463 67 (1977), the contents of which are incorporated by reference herein in their entirety. Another conventional sequencing method involves chemical degradation of nucleic acid fragments. See, Maxam et al., Proc. Natl. Acad. Sci., 74: 560 564 (1977), the contents of which are incorporated by reference herein in their entirety. Methods have also been developed based upon sequencing by hybridization. See, e.g., Harris et al., (U.S. patent application number 2009/0156412), the contents of which are incorporated by reference herein in their entirety.

A sequencing technique that can be used in the methods of the provided invention includes, for example, Helicos True Single Molecule Sequencing (tSMS) (Harris T. D. et al. (2008) Science 320:106-109), the contents of which are incorporated by reference herein in their entirety. Further description of tSMS is shown, for example, in Lapidus et al. (U.S. Pat. No. 7,169,560), the contents of which are incorporated by reference herein in their entirety, Lapidus et al. (U.S. patent application publication number 2009/0191565, the contents of which are incorporated by reference herein in their entirety), Quake et al. (U.S. Pat. No. 6,818,395, the contents of which are incorporated by reference herein in their entirety), Harris (U.S. Pat. No. 7,282,337, the contents of which are incorporated by reference herein in their entirety), Quake et al. (U.S. patent application publication number 2002/0164629, the contents of which are incorporated by reference herein in their entirety), and Braslaysky, et al., PNAS (USA), 100: 3960-3964 (2003), the contents of which are incorporated by reference herein in their entirety.

Another example of a DNA sequencing technique that can be used in the methods of the provided invention is 454 sequencing (Roche) (Margulies, M et al. 2005, Nature, 437, 376-380, the contents of which are incorporated by reference herein in their entirety). Another example of a DNA sequencing technique that can be used in the methods of the provided invention is SOLiD technology (Applied Biosystems). Another example of a DNA sequencing technique that can be used in the methods of the provided invention is Ion Torrent sequencing (U.S. patent application publication numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the contents of each of which are incorporated by reference herein in their entirety).

In some embodiments, the sequencing technology is Illumina sequencing. Illumina sequencing is based on the amplification of DNA on a solid surface using fold-back PCR and anchored primers. Genomic DNA can be fragmented, or in the case of cfDNA, fragmentation is not needed due to the already short fragments. Adapters are ligated to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. Yet another example of a sequencing technique that can be used in the methods of the provided invention is nanopore sequencing (Soni G V and Meller A. (2007) Clin Chem 53: 1996-2001, the contents of which are incorporated by reference herein in their entirety). Another example of a sequencing technique that can be used in the methods of the provided invention involves using a chemical-sensitive field effect transistor (chemFET) array to sequence DNA (for example, as described in US Patent Application Publication No. 20090026082, the contents of which are incorporated by reference herein in their entirety). Another example of a sequencing technique that can be used in the methods of the provided invention involves using an electron microscope (Moudrianakis E. N. and Beer M. Proc Natl Acad Sci USA. 1965 March; 53:564-71, the contents of which are incorporated by reference herein in their entirety).

If the nucleic acid from the sample is degraded or only a minimal amount of nucleic acid can be obtained from the sample, PCR can be performed on the nucleic acid in order to obtain a sufficient amount of nucleic acid for sequencing (See, e.g., Mullis et al. U.S. Pat. No. 4,683,195, the contents of which are incorporated by reference herein in its entirety).

Figure 5A:
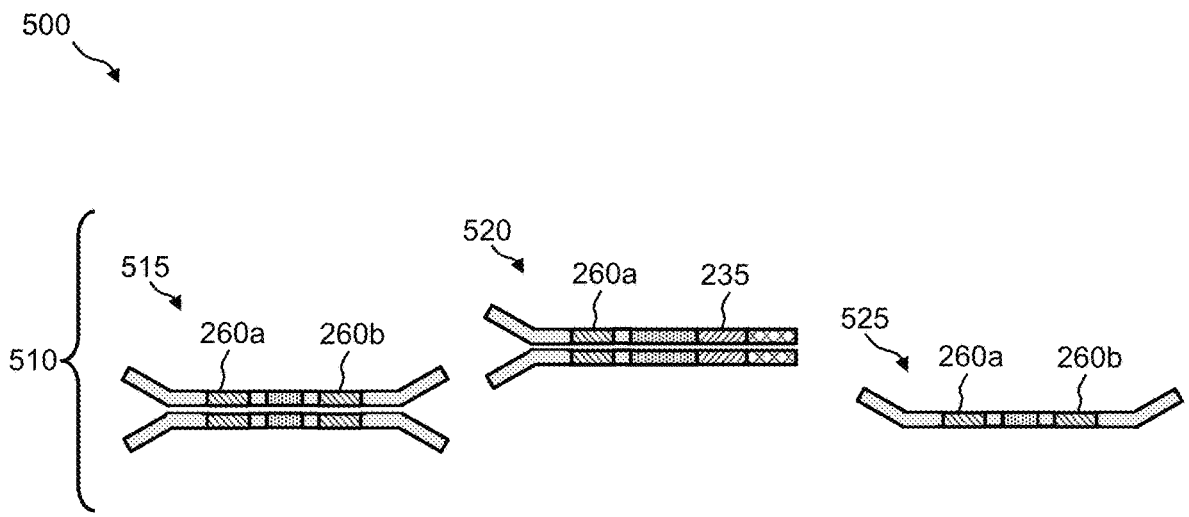
FIGS. 5A and 5B illustrate a process of separating sequencing reads as derived from dsDNA or ssDNA based on unique sequence tags.
Figure 5B:
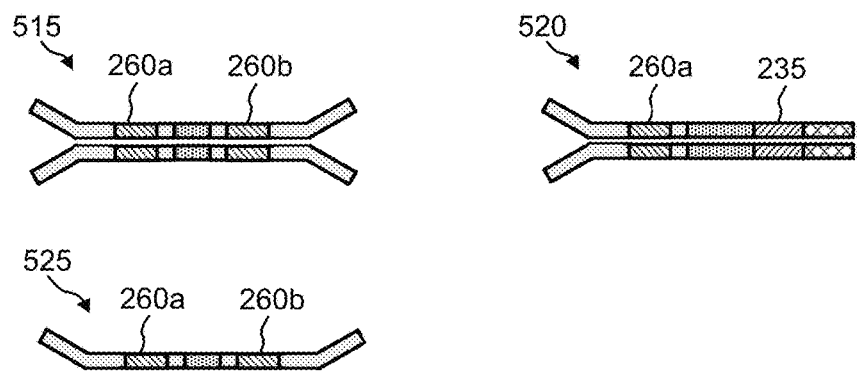

FIGS. 5A and 5B illustrate an example of a process 500 for separating sequencing reads as derived from dsDNA or ssDNA based on unique sequence tags (e.g., a barcode, UMI or index sequences). Process 500 may include, but is not limited to, the following steps.

In a first step and referring now to FIG. 5A, a sequencing library 510 is prepared from a cfDNA sample and sequenced. In one example, the cfDNA sequencing library 510 is prepared using method 100 of FIG. 1. cfDNA sequencing library 510 includes, for example, a first amplicon 515 derived from dsDNA, a second amplicon 520 derived from ssDNA, and a third amplicon 525 derived from the intact strand of nicked dsDNA. First amplicon 515 includes first and second unique sequence tags 260a and 260b, the second amplicon 520 includes UMI region 260a and single-strand specific sequence tag 235, and third amplicon 525 includes first and second unique sequence tags 260a and 260b.

In a next step and referring now to FIG. 5B, sequence reads from amplicons 515, 520, and 525 are identified and classified as being originally derived either from dsDNA (first and second unique sequence tags 260a and 260b) or as being originally derived from ssDNA (single-strand specific tag 235). In one embodiment, process 500 (depicted in FIG. 5A) is used for differential counting of double-stranded fragments and single-stranded fragments in a cfDNA sample.

Figure 6A:
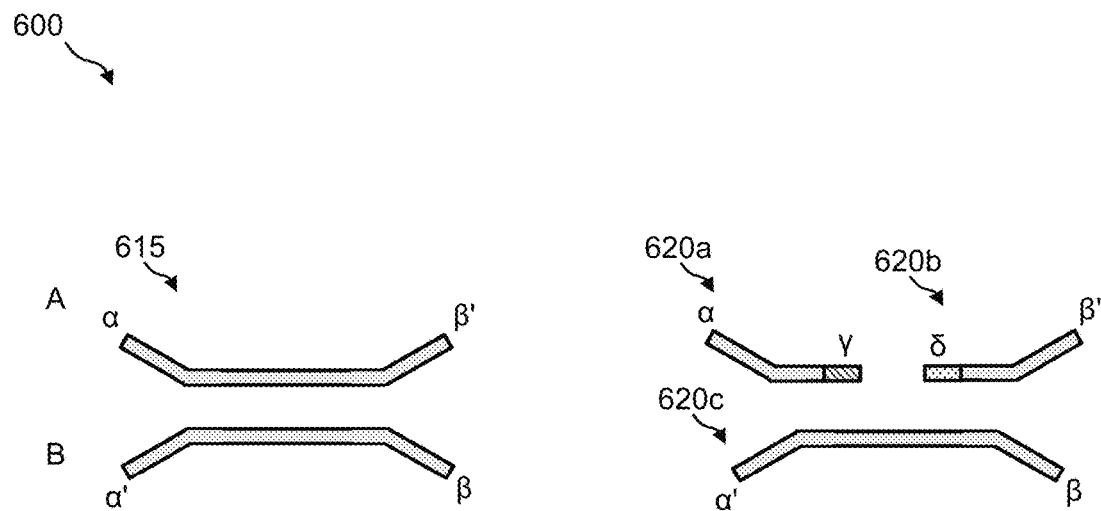
FIGS. 6A and 6B illustrate a process for identifying and classifying sequence reads from a cfDNA sample and obtaining fragment size information and genome position associated with sequencing reads from nicked dsDNA fragments in a cfDNA sample.
Figure 6B:
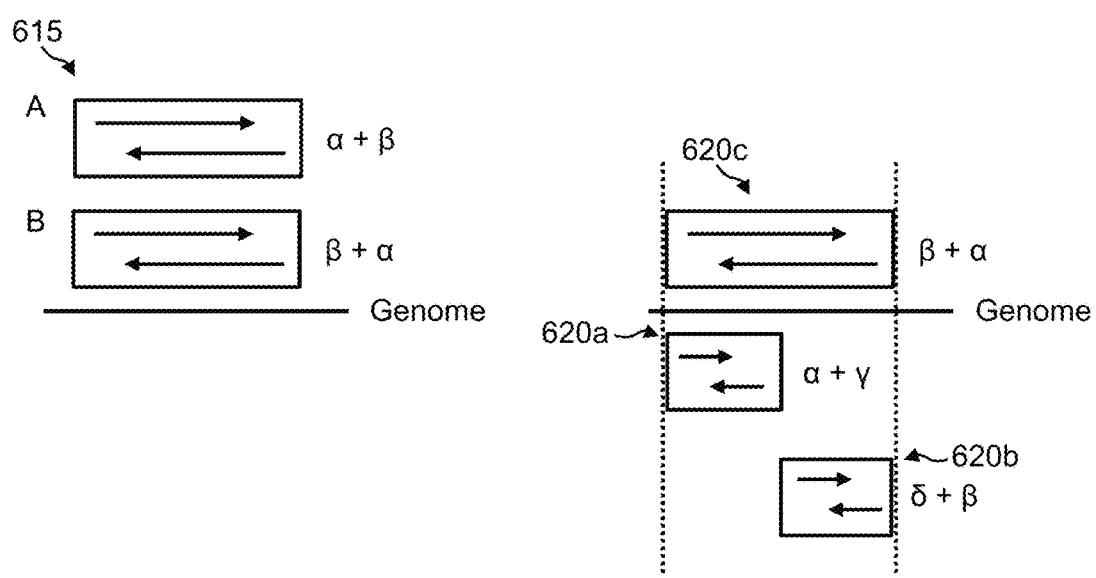

FIGS. 6A and 6B illustrate an example of a process 600 for identifying and classifying sequence reads from a cfDNA sample. In one embodiment, process 600 maintains original fragment size information and genome position associated with sequencing reads from nicked dsDNA fragments in a cfDNA sample. In one example, process 600 is used to obtain fragment size information from nicked dsDNA fragments in a sequencing library prepared from a cfDNA sample using method 300, as illustrated in FIG. 3 and FIGS. 4A and 4B. In this example, first and second unique sequence tags 260a and 260b of Y-adapters (see, e.g., 255 of FIG. 4A) are designated as "α" and "β", respectively; and the unique sequence tags on the dsDNA nicked fragments are designated as "γ" and "δ".

In a first step of an example process, and referring now to FIG. 6A, sequencing reads are obtained from amplicon 615 derived from intact dsDNA molecule and from amplicons 620a, 620b, and 620c derived from a nicked dsDNA molecule. Sequence reads from one strand (A) of amplicon 615 include sequence tags α and β' and the other strand (B) includes sequence tags α' and β. For the sequence reads from the nicked dsDNA molecule, sequence reads from amplicon 620a include sequence tags α and γ; sequence reads from amplicon 620b include sequence tags δ and β; and sequence reads from amplicon 620c include sequence tags α and β.

In a next step and referring now to FIG. 6B, for the intact dsDNA molecule, sequence reads from amplicon 615 are aligned to a reference genome. One strand (A) of amplicon 615 forms a sequence read including unique sequence tags α and β (i.e., in an α+β orientation) and the other strand (B) forms a sequence read including unique sequence tags β and α (i.e., in a β+α orientation). The sequence information from both strands (i.e., A and B) can be merged to form a high-quality sequence read.

Referring still to FIG. 6B, for the nicked dsDNA molecule, sequence reads from amplicon 620a, 620b, and 620c are aligned to a reference genome. Sequence reads from amplicon 620c represent the complete sequence of amplicon 620c (which includes unique sequence tags α and β). Sequence reads from amplicons 620a (which includes unique sequence tags α+γ) and 620b (which includes unique sequence tags δ+β), and which represent the sequence reads for the nicked dsDNA fragments that are complementary portions of amplicon 620c. In one embodiment, to obtain fragment size and genomic position information associated with the nicked dsDNA fragment, the ends of the reads from amplicons 620a and 620b can be aligned (indicated by dotted lines) with the ends of the sequence reads from amplicon 620c, such that the sequences from the α sequence tags are shared on one end and the sequence reads from the β sequence tags are shared on the other end.

Biological Samples

Aspects of the invention involve obtaining a sample, e.g., a biological sample, such as a tissue and/or body fluid sample, from a subject for purposes of analyzing a plurality of nucleic acids (e.g., a plurality of cfDNA molecules) therein. Samples in accordance with embodiments of the invention can be collected in any clinically-acceptable manner. Any sample suspected of containing a plurality of nucleic acids can be used in conjunction with the methods of the present invention. In some embodiments, a sample can comprise a tissue, a body fluid, or a combination thereof. In some embodiments, a biological sample is collected from a healthy subject. In some embodiments, a biological sample is collected from a subject who is known to have a particular disease or disorder (e.g., a particular cancer or tumor). In some embodiments, a biological sample is collected from a subject who is suspected of having a particular disease or disorder.

As used herein, the term "tissue" refers to a mass of connected cells and/or extracellular matrix material(s). Non-limiting examples of tissues that are commonly used in conjunction with the present methods include skin, hair, finger nails, endometrial tissue, nasal passage tissue, central nervous system (CNS) tissue, neural tissue, eye tissue, liver tissue, kidney tissue, placental tissue, mammary gland tissue, gastrointestinal tissue, musculoskeletal tissue, genitourinary tissue, bone marrow, and the like, derived from, for example, a human or non-human mammal. Tissue samples in accordance with embodiments of the invention can be prepared and provided in the form of any tissue sample types known in the art, such as, for example and without limitation, formalin-fixed paraffin-embedded (FFPE), fresh, and fresh frozen (FF) tissue samples.

As used herein, the term "body fluid" refers to a liquid material derived from a subject, e.g., a human or non-human mammal. Non-limiting examples of body fluids that are commonly used in conjunction with the present methods include mucous, blood, plasma, serum, serum derivatives, synovial fluid, lymphatic fluid, bile, phlegm, saliva, sweat, tears, sputum, amniotic fluid, menstrual fluid, vaginal fluid, semen, urine, cerebrospinal fluid (CSF), such as lumbar or ventricular CSF, gastric fluid, a liquid sample comprising one or more material(s) derived from a nasal, throat, or buccal swab, a liquid sample comprising one or more materials derived from a lavage procedure, such as a peritoneal, gastric, thoracic, or ductal lavage procedure, and the like.

In some embodiments, a sample can comprise a fine needle aspirate or biopsied tissue. In some embodiments, a sample can comprise media containing cells or biological material. In some embodiments, a sample can comprise a blood clot, for example, a blood clot that has been obtained from whole blood after the serum has been removed. In some embodiments, a sample can comprise stool. In one preferred embodiment, a sample is drawn whole blood. In one aspect, only a portion of a whole blood sample is used, such as plasma, red blood cells, white blood cells, and platelets. In some embodiments, a sample is separated into two or more component parts in conjunction with the present methods. For example, in some embodiments, a whole blood sample is separated into plasma, red blood cell, white blood cell, and platelet components.

In some embodiments, a sample includes a plurality of nucleic acids not only from the subject from which the sample was taken, but also from one or more other organisms, such as viral DNA/RNA that is present within the subject at the time of sampling.

Nucleic acid can be extracted from a sample according to any suitable methods known in the art, and the extracted nucleic acid can be utilized in conjunction with the methods described herein. See, e.g., Maniatis, et al., Molecular Cloning: A Laboratory Manual, Cold Spring Harbor, N.Y., pp. 280-281, 1982, the contents of which are incorporated by reference herein in their entirety.

In one preferred embodiment, cell free nucleic acid (e.g., cfDNA) is extracted from a sample. cfDNA are short base nuclear-derived DNA fragments present in several bodily fluids (e.g. plasma, stool, urine). See, e.g., Mouliere and Rosenfeld, PNAS 112(11): 3178-3179 (March 2015); Jiang et al., PNAS (March 2015); and Mouliere et al., Mol Oncol, 8(5):927-41 (2014). Tumor-derived circulating tumor DNA (ctDNA) constitutes a minority population of cfDNA, in some cases, varying up to about 50%. In some embodiments, ctDNA varies depending on tumor stage and tumor type. In some embodiments, ctDNA varies from about 0.001% up to about 30%, such as about 0.01% up to about 20%, such as about 0.01% up to about 10%. The covariates of ctDNA are not fully understood, but appear to be positively correlated with tumor type, tumor size, and tumor stage. E.g., Bettegowda et al, Sci Trans Med, 2014; Newmann et al, Nat Med, 2014. Despite the challenges associated with the low population of ctDNA in cfDNA, tumor variants have been identified in ctDNA across a wide span of cancers. E.g., Bettegowda et al, Sci Trans Med, 2014. Furthermore, analysis of cfDNA versus tumor biopsy is less invasive, and methods for analyzing, such as sequencing, enable the identification of sub-clonal heterogeneity. Analysis of cfDNA has also been shown to provide for more uniform genome-wide sequencing coverage as compared to tumor tissue biopsies. In some embodiments, a plurality of cfDNA is extracted from a sample in a manner that reduces or eliminates co-mingling of cfDNA and genomic DNA. For example, in some embodiments, a sample is processed to isolate a plurality of the cfDNA therein in less than about 2 hours, such as less than about 1.5, 1 or 0.5 hours.

A non-limiting example of a procedure for preparing nucleic acid from a blood sample follows. Blood may be collected in 10 mL EDTA tubes (for example, the BD VACUTAINER® family of products from Becton Dickinson, Franklin Lakes, New Jersey), or in collection tubes that are adapted for isolation of cfDNA (for example, the CELL FREE DNA BCT® family of products from Streck, Inc., Omaha, Nebraska) can be used to minimize contamination through chemical fixation of nucleated cells, but little contamination from genomic DNA is observed when samples are processed within 2 hours or less, as is the case in some embodiments of the present methods. Beginning with a blood sample, plasma may be extracted by centrifugation, e.g., at 3000 rpm for 10 minutes at room temperature minus brake. Plasma may then be transferred to 1.5 ml tubes in 1 ml aliquots and centrifuged again at 7000 rpm for 10 minutes at room temperature. Supernatants can then be transferred to new 1.5 ml tubes. At this stage, samples can be stored at −80° C. In certain embodiments, samples can be stored at the plasma stage for later processing, as plasma may be more stable than storing extracted cfDNA.

Plasma DNA can be extracted using any suitable technique. For example, in some embodiments, plasma DNA can be extracted using one or more commercially available assays, for example, the QIAmp Circulating Nucleic Acid Kit family of products (Qiagen N.V., Venlo Netherlands). In certain embodiments, the following modified elution strategy may be used. DNA may be extracted using, e.g., a QIAmp Circulating Nucleic Acid Kit, following the manufacturer's instructions (maximum amount of plasma allowed per column is 5 mL). If cfDNA is being extracted from plasma where the blood was collected in Streck tubes, the reaction time with proteinase K may be doubled from 30 min to 60 min. Preferably, as large a volume as possible should be used (i.e., 5 mL). In various embodiments, a two-step elution may be used to maximize cfDNA yield. First, DNA can be eluted using 30 μL of buffer AVE for each column. A minimal amount of buffer necessary to completely cover the membrane can be used in the elution in order to increase cfDNA concentration. By decreasing dilution with a small amount of buffer, downstream desiccation of samples can be avoided to prevent melting of double stranded DNA or material loss. Subsequently, about 30 μL of buffer for each column can be eluted. In some embodiments, a second elution may be used to increase DNA yield.

Computer Systems and Devices

Aspects of the invention described herein can be performed using any type of computing device, such as a computer, that includes a processor, e.g., a central processing unit, or any combination of computing devices where each device performs at least part of the process or method. In some embodiments, systems and methods described herein may be performed with a handheld device, e.g., a smart tablet, or a smart phone, or a specialty device produced for the system.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer programs include, by way of example, both general and special purpose microprocessors, and any one or more processors of any kind of digital computer. Generally, a processor will receive instructions and data from a read-only memory or a random access memory, or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including, by way of example, semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through a network by any form or medium of digital data communication, e.g., a communication network. For example, a reference set of data may be stored at a remote location and a computer can communicate across a network to access the reference data set for comparison purposes. In other embodiments, however, a reference data set can be stored locally within the computer, and the computer accesses the reference data set within the CPU for comparison purposes. Examples of communication networks include, but are not limited to, cell networks (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, a data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification (RFID) tags or chips, or any other medium that can be used to store the desired information, and which can be accessed by a computing device.

Functions described herein can be implemented using software, hardware, firmware, hardwiring, or combinations of any of these. Any of the software can be physically located at various positions, including being distributed such that portions of the functions are implemented at different physical locations.

As one skilled in the art would recognize as necessary or best-suited for performance of the methods of the invention, a computer system for implementing some or all of the described inventive methods can include one or more processors (e.g., a central processing unit (CPU) a graphics processing unit (GPU), or both), main memory and static memory, which communicate with each other via a bus.

A processor will generally include a chip, such as a single core or multi-core chip, to provide a central processing unit (CPU). A process may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system. Preferably, each computer includes a non-transitory memory such as a solid state drive, flash drive, disk drive, hard drive, etc.

While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to, one or more solid-state memories (e.g., subscriber identity module (SIM) card, secure digital card (SD card), micro SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Any of the software can be physically located at various positions, including being distributed such that portions of the functions are implemented at different physical locations.

Additionally, systems of the invention can be provided to include reference data. Any suitable genomic data may be stored for use within the system. Examples include, but are not limited to: comprehensive, multi-dimensional maps of the key genomic changes in major types and subtypes of cancer from The Cancer Genome Atlas (TCGA); a catalog of genomic abnormalities from The International Cancer Genome Consortium (ICGC); a catalog of somatic mutations in cancer from COSMIC; the latest builds of the human genome and other popular model organisms; up-to-date reference SNPs from dbSNP; gold standard indels from the 1000 Genomes Project and the Broad Institute; exome capture kit annotations from Illumina, Agilent, Nimblegen, and Ion Torrent; transcript annotations; small test data for experimenting with pipelines (e.g., for new users).

In some embodiments, data is made available within the context of a database included in a system. Any suitable database structure may be used including relational databases, object-oriented databases, and others. In some embodiments, reference data is stored in a relational database such as a "not-only SQL" (NoSQL) database. In certain embodiments, a graph database is included within systems of the invention. It is also to be understood that the term "database" as used herein is not limited to one single database; rather, multiple databases can be included in a system. For example, a database can include two, three, four, five, six, seven, eight, nine, ten, fifteen, twenty, or more individual databases, including any integer of databases therein, in accordance with embodiments of the invention. For example, one database can contain public reference data, a second database can contain test data from a patient, a third database can contain data from healthy individuals, and a fourth database can contain data from sick individuals with a known condition or disorder. It is to be understood that any other configuration of databases with respect to the data contained therein is also contemplated by the methods described herein.

References and citations to other documents, such as patents, patent applications, patent publications, journals, books, papers, web contents, have been made throughout this disclosure. All such documents are hereby incorporated herein by reference in their entirety for all purposes.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof. All references cited throughout the specification are expressly incorporated by reference herein.

The foregoing detailed description of embodiments refers to the accompanying drawings, which illustrate specific embodiments of the present disclosure. Other embodiments having different structures and operations do not depart from the scope of the present disclosure. The term "the invention"

or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

While the present invention has been described with reference to the specific embodiments thereof, it should be understood by those skilled in the art that various changes may be made and equivalents may be substituted without departing from the true spirit and scope of the invention. In addition, many modifications may be made to adapt to a particular situation, material, composition of matter, process, process step or steps, to the objective, spirit and scope of the present invention. All such modifications are intended to be within the scope of the claims appended hereto.

The invention claimed is:

1. A method for preparing a cell-free DNA (cfDNA) sequencing library from a cfDNA sample comprising a plurality of double-stranded DNA (dsDNA), nicked dsDNA, and single-stranded DNA (ssDNA) molecules, the method comprising:
    extending, using a strand-displacing polymerase, a nicked dsDNA molecule to produce an ssDNA molecule;
    ligating a universal adapter comprising a unique sequence tag to the ssDNA molecule;
    extending the universal adapter to generate a nicked-ssDNA-derived dsDNA molecule; and
    generating a cfDNA sequencing library from the nicked-ssDNA-derived dsDNA molecule.

2. The method according to claim 1, further comprising ligating a sequencing Y-adapter to the nicked-ssDNA-derived dsDNA molecule before generating the cfDNA sequencing library.

3. The method according to claim 2, wherein the sequencing Y-adapter comprises a unique sequence tag.

4. The method according to claim 1, further comprising:
    ligating a first sequencing Y-adapter to a first end of an intact dsDNA molecule in the cfDNA sample; and
    ligating a second sequencing Y-adapter to a second end of the intact dsDNA molecule;
    generating a cfDNA sequencing library from the intact dsDNA molecule.

5. The method according to claim 4, wherein the first sequencing Y-adapter comprises a first unique sequence tag, and the second sequencing Y-adapter comprises a second unique sequence tag.

6. The method according to claim 5, wherein the first and the second unique sequence tags are the same.

7. The method according to claim 5, wherein the first and the second unique sequence tags are different.

8. The method according to claim 1, wherein one or more of the unique sequence tags comprises a universal primer and at least one of a molecular barcode sequence, a unique molecular identifier (UMI), or an index sequence.

9. The method according to claim 1, wherein one or more of the universal adapters comprises an adenylated 5' end.

10. The method according to claim 1, wherein one or more of the universal adapters comprises a blocked or a phosphorylated 3' end.

11. The method according to claim 1, further comprising performing an end repair reaction on a dsDNA molecule.

12. The method according to claim 1, wherein generating the cfDNA sequencing library comprises performing a PCR amplification reaction.

13. The method according to claim 1, wherein the cfDNA sample is isolated from a plasma fraction of a blood sample.

* * * * *